United States Patent
de Voir et al.

(10) Patent No.: US 7,761,163 B2
(45) Date of Patent: Jul. 20, 2010

(54) ATRIAL HEART STIMULATOR APPARATUS AND METHOD

(75) Inventors: Christopher S. de Voir, Tigard, OR (US); Jie Lian, Beaverton, OR (US); Richard A. Schomburg, Hillsboro, OR (US); Duane Patterson, Tigard, OR (US); Hannes Kraetschmer, West Linn, OR (US); Dirk Muessig, West Linn, OR (US)

(73) Assignee: Biotronik CRM Patent AG, Baar (CH)

( * ) Notice: Subject to any disclaimer, the term of this patent is extended or adjusted under 35 U.S.C. 154(b) by 633 days.

(21) Appl. No.: 11/451,138

(22) Filed: Jun. 12, 2006

(65) Prior Publication Data

US 2007/0288063 A1     Dec. 13, 2007

(51) Int. Cl.
*A61N 1/362* (2006.01)
(52) U.S. Cl. .............................. 607/28; 607/9; 607/14
(58) Field of Classification Search ............ 607/9, 607/14, 28
See application file for complete search history.

(56) References Cited

U.S. PATENT DOCUMENTS

| | | | |
|---|---|---|---|
| 5,273,035 A | 12/1993 | Markowitz et al. | |
| 5,846,264 A * | 12/1998 | Andersson et al. | 607/28 |
| 5,954,755 A | 9/1999 | Casavont | |
| 6,553,259 B2 * | 4/2003 | Mouchawar et al. | 607/11 |
| 2005/0021095 A1 | 1/2005 | Rueter et al. | |
| 2005/0222630 A1 | 10/2005 | Schermeier et al. | |

OTHER PUBLICATIONS

European Search Report, dated Oct. 15, 2007.

* cited by examiner

*Primary Examiner*—Carl H Layno
*Assistant Examiner*—Deborah Malamud
(74) *Attorney, Agent, or Firm*—ARC IP Law, PC; Joseph J. Mayo

(57) ABSTRACT

The invention relates to heart stimulators and implantable atrial pacemakers which utilize a rhythm based atrial capture threshold test wherein in a ventricle based DDI mode a predetermined number of ventricle started atrial and ventricular escape intervals are triggered with an overdrive rate about 20% higher than an intrinsic heart rate. The number of atrial sense events during atrial capture threshold test is counted. Too high of a number of atrial sense events indicates loss of capture due to too small of a pulse strength of the atrial stimulation pulses.

15 Claims, 6 Drawing Sheets

ATRIAL HEART STIMULATOR APPARATUS AND METHOD

BACKGROUND OF THE INVENTION

1. Field of the Invention

Embodiments of the invention described herein pertain to the field of medical apparatus and methods. More particularly, but not by way of limitation, one or more embodiments of the invention generally relate to a heart stimulator for pacing at least an atrium of a heart by delivery of electrical stimulation pulses to the atrium and more specifically relate to an atrial heart stimulator that provides automatic atrial capture threshold testing.

2. Description of the Related Art

Typically, an atrial heart stimulator is an implantable dual-chamber pacemaker providing a stimulation pulse generator for generating atrial stimulation pulses to be delivered to an atrium of a heart and ventricular stimulation pulses to be delivered to a ventricle of a heart. In general, a dual chamber pacemaker provides a separate stimulation pulse generator for each heart chamber to be stimulated. However, the use of a single switchable stimulation pulse generator is also possible.

Heart stimulators like pacemakers deliver stimulation pulses (also called pacing pulses) to the heart to cause the stimulated heart chamber to contract if no natural (intrinsic) contraction of the heart chamber occurs. A stimulation pulse for delivery to the myocardium (heart tissue) of the atrium of a heart is called an atrial stimulation pulse or an atrial pace Ap. Likewise, a stimulation pulse for delivery to a ventricle of a heart is called a ventricular stimulation pulse or a ventricular pace Vp.

In order to enable the heart stimulator to detect intrinsic contractions of a heart chamber, a demand pacemaker usually comprises a sensing channel comprising sense amplifiers for processing electrical signals originating from a respective heart chamber in order to detect electrical signals corresponding to a depolarization of the heart tissue that is followed by a natural contraction of the heart.

Atrial and ventricular stimulation pulse generators and atrial and ventricular sensing channels are connected to or are connectable to electrode leads having electrodes for placement in a respective heart chamber. The electrodes connected to a stimulation pulse generator serve for delivery of stimulation pulses to the heart tissue whereas the electrodes connected to a respective sensing channel serve for picking up electrical signals from the heart tissue.

A control unit triggers the generation of a respective atrial or ventricular stimulation pulse according to a pre-programmed, variable timing regime in order to provide for adequate timing of the stimulation pulses.

Depending on the mode of operation, a pacemaker delivers a stimulation pulse (pacing pulse) to a heart chamber (atrium or ventricle) only if needed, that is, if no natural excitation of that chamber occurs. Such a mode of operation is called an inhibited or demand mode of operation since the delivery of a stimulation pulse is inhibited if a natural excitation of the heart chamber is sensed within a predetermined time interval (usually called escape interval) so the heart chamber is only stimulated if demanded.

In the demand mode, the pacemakers monitors the heart chamber to be stimulated in order to determine if a cardiac excitation (heartbeat) has naturally occurred. Such natural (non-stimulated) excitation, also referred to as "intrinsic" or "sinus" cardiac activity, are manifested by the occurrence of recognizable electrical signals that accompany the depolarization or excitation of a cardiac muscle tissue (myocardium). The depolarization of the myocardium is usually immediately followed by a cardiac contraction. For the purpose of the present application, depolarization and contraction may be considered as simultaneous events and the terms "depolarization" and "contraction" are used herein as synonyms. The recognizable electrical signals that accompany the depolarization or excitation of a heart chamber are picked up (sensed) by the atrial or the ventricular sensing channel, respectively.

A natural contraction of a heart chamber can be detected by evaluating electrical signals sensed by the sensing channels. In the sensed electrical signal the depolarization of an atrium muscle tissue is manifested by occurrence of a signal known as "P-wave". Similarly, the depolarization of ventricular muscle tissue is manifested by the occurrence of a signal known as "R-wave". A P-wave or an R-wave signal represents an atrial event or a ventricular event, respectively, in the further course of this application.

In a demand mode of operation, the pacemaker monitors the heart for the occurrence of P-waves and/or R-waves. If such signals are sensed within a prescribed time period or time window, which is called atrial or ventricular escape interval, respectively, then the escape interval is reset (i.e., restarted) and generation of a stimulation pulse is inhibited and no unnecessary stimulation pulse is triggered. The escape interval is measured from the last heartbeat, i.e., from the last occurrence of an intrinsic (sensed) atrial event (P-wave, A-sense, AS) if the atrium is monitored, or an intrinsic (sensed) ventricular event (R-wave, V-sense, VS) if the ventricle is monitored, or the generation of a stimulation pulse (V-pace, VP; A-pace, AP) if no respective intrinsic event has occurred. If the escape interval "times-out", i.e., if a time period equal to the escape interval has elapsed without the sensing of a P-wave and/or R-wave (depending upon which chamber of the heart is being monitored), then a stimulation pulse is triggered at the conclusion of the escape interval. In this way, the pacemaker provides stimulation pulses "on demand," i.e., only as needed, when intrinsic cardiac activity does not occur within the prescribed escape interval.

Several modes of operation are available in a state of the art multi mode pacemaker. The pacing modes of a pacemaker, both single and dual or more chamber pacemakers, are classified by type according to a three letter code. According to this code, the first letter identifies the chamber of the heart that is paced (i.e., that chamber where a stimulation pulse is delivered), with a "V" indicating the ventricle, an "A" indicating the atrium, and a "D" indicating both the atrium and ventricle. The second letter of the code identifies the chamber wherein cardiac activity is sensed, using the same letters, and wherein an "O" indicates no sensing occurs. The third letter of the code identifies the action or response that is taken by the pacemaker. In general, three types of action or responses are recognized:

(1) an Inhibiting ("I") response wherein a stimulation pulse is triggered for the designated chamber at the conclusion of the appropriate escape interval unless cardiac activity is sensed during the escape interval, in which case the stimulation pulse is inhibited;

(2) a Trigger ("T") response wherein a stimulation pulse to a prescribed chamber of the heart is triggered a prescribed period of time after a sensed event (i.e. triggering of a ventricular stimulation pulse at the end of an AV-interval that is started (Triggered) by an atrial sense or pacing event); or (3) a Dual ("D") response wherein both the Inhibiting mode and Trigger mode may be evoked, e.g., with the "inhibiting" occurring in one chamber of the heart and the "triggering" in the other, i.e. when an atrial sense event inhibits triggering of an atrial stimulation pulse at the end of an atrial escape interval and at the same time starts (triggers) a next ventricular and atrial escape interval.

An additional fourth letter "R" may be added to the basic three letter code to designate a rate-responsive pacemaker and/or whether the rate-responsive features of such a rate-responsive pacemaker are enabled ("O" typically being used to designate that rate-responsive operation has been disabled). A rate-responsive pacemaker is one wherein a specified parameter or combination of parameters, such as physical activity, the amount of oxygen in the blood, the temperature of the blood, etc., is sensed with an appropriate sensor and is used as a physiological indicator of what the pacing rate should be. When enabled, such rate-responsive pacemaker thus provides stimulation pulses that best meet the physiological demands of the patient.

Multiple-mode, demand-type, cardiac pacemakers allow a sequence of contractions of the heart's chamber which equals as far as possible a natural behavior of the healthy heart for damaged or diseased hearts that are unable to do so on their own.

In a healthy heart, initiation of the cardiac cycle normally begins with depolarization of the sinoatrial (SA) node. This specialized structure is located in the upper portion of the right atrium wall and acts as a natural "pacemaker" of the heart. In a normal cardiac cycle and in response to the initiating SA depolarization, the atrium contracts and forces the blood that has accumulated therein into the ventricle. The natural stimulus causing the atrium to contract is conducted to ventricle via the atrioventricular node (AV node) with a short, natural delay, the atrioventricular delay (AV-delay). Thus a short time after an atrial contraction (a time sufficient to allow the bulk of the blood in the atrium to flow through the one-way valve into the ventricle), the ventricle contracts, forcing the blood out of the ventricle to body tissue. A typical time interval between contraction of the atrium and contraction of the ventricle might be 180 ms; a typical time interval between contraction of the ventricle and the next contraction of the atrium might be 800 ms. Thus, in a healthy heart providing proper AV– synchrony an atrial contraction (A) is followed a relatively short time thereafter by a ventricle contraction (V), that in turn is followed a relatively long time thereafter by the next atrial contraction and so on. Where AV synchrony exists, the heart functions very efficiently as a pump in delivering life-sustaining blood to body tissue; where AV synchrony is absent, the heart functions as an inefficient pump.

To mimic the natural behavior of a heart, a dual-chamber pacemaker, in conventional manner, defines a basic atrial escape interval (AEI) that sets the time interval for scheduling an atrial stimulation pulse. The atrial escape interval can be started by a ventricular event and end with an atrial event. A basic AV delay (AVD) or ventricular escape interval (VEI) sets the time interval or delay between an atrial event and a ventricular event. In such embodiment, AEI and AVD (or VEI) thus together define a length of a heart cycle which is reciprocal to the pacing rate at which stimulation pulses are generated and delivered to a patient's heart in the absence of sensed natural cardiac activity.

For the purpose of this application, a "ventricular event" (V) may refer either a natural ventricular excitation (intrinsic ventricular event; Vs) which is sensed as an R-wave or a ventricular stimulation pulse (V-pulse, Vp). Similarly, an atrial event (A) shall refer to both, a P-wave (A-sense; As) or an atrial stimulation pulse (A-pulse, Ap).

Dual chamber pacing often times is in a DDD mode of operation of the pacemaker.

In general, there are two kinds of dual-chamber DDD-timing schemes:

In atrial-based DDD pacing, all timing is controlled either from the sensing of atrial activity (a P-wave; A-sense; As) or an atrial pacing (Ap). When a P-wave (Vs) is sensed, two separate timers are started that operate in parallel. A first timer defines an atrial escape interval (A-Ap), which, if timed-out, results in an atrial paced event (Ap). A second timer defines a separate AV delay, which, if timed-out, results in a ventricular paced event (Vp). The first and second timers both start upon sensed or paced atrial activity (A). The AV delay timer does not affect the basic atrial escape interval timer. The atrial escape interval timer thus controls the basic functioning rate of the pacemaker from atrial to atrial event. The ventricle is paced, if needed, at a rate that tracks the sensed atrial rate. If no atrial activity is sensed, then the atrium is also paced at a rate equal to the set rate. Nonetheless, even when operating in such atrial-based mode, there still remains a need to enhance pacemaker longevity, as well as a need to allow the heart to beat at its own rhythm more often.

In atrial based DDD-pacing the atrial escape interval usually is an A-A-interval which is simultaneously started with a ventricular escape interval (AV-interval)

As an alternative to above-described atrial-based DDD pacing, there is also a second type of dual chamber operation known as ventricular-based pacing. In ventricular-based DDD pacing (sometimes referred to as ventricular-based timing), two parallel timers are used, as indicated above. By a ventricular event, a VA Delay timer is started. If the VA Delay timer times out all the way, an atrial pulse (Ap) is provided. Thus, the VA-delay timer defines an atrial escape interval (AEI). If a P-wave is sensed before the VA Delay timer times-out, such sensing terminates the VA Delay timer. The sensing of a P-wave or the generating of an A-pulse thus defines an atrial event. A ventricular event also starts a Ventricular Escape Interval timer. If this Ventricular Escape Interval timer times-out all the way, a ventricular pulse (Vp) is provided. If an R-wave is sensed before the Ventricular Escape Interval timer times-out, such sensing terminates the Ventricular Escape Interval Timer. The sensing of an R-wave (V-sense; Vs) or the generating of ventricular pulse thus comprise a ventricular event (V), and this ventricular event (V) starts both the VA Delay timer and the Ventricular Escape Interval Timer again.

In patients having an AV-block, the natural conduction from the atrium to the ventricle is affected. However, the atrium itself may contract in a natural way with a physiologically adequate rate. In the DDD(R) mode of operation an AV-sequential stimulation or atrium-synchronous pacing is possible, which allows tracking of intrinsic atrial contractions and to stimulate the ventricle with an (artificial) AV delay after each sensed atrial contraction in order to maintain AV synchronicity. In such mode of operation the maximum AV delay between an atrial event and the next paced ventricular event is given by the ventricular escape interval.

The choice of an adequate duration of an escape interval depends at least on two demands: the escape interval shall reflect the natural timing of a healthy heart. Therefore, the ventricular escape interval would be chosen to match the natural atrioventricular conduction time in a healthy heart. On the other hand, it is an object to allow as many natural contractions of a heart chamber as possible. Therefore, timeout of the escape interval should not occur too early to give the heart the chance to contract on its own.

To meet these demands one of the programmable modes that has been used with programmable pacemakers for many years is a mode known as the "hysteresis" mode. The hysteresis mode is used in conjunction with selected other modes, such as single-chamber demand pacing, to allow the natural sinus rhythm of the heart to persist at rates less than the programmed minimum rate of the pacemaker. The programmed minimum rate of the pacemaker, in turn, sets the atrial escape interval. During pacing, i.e., during those times when the pacemaker is generating stimulation pulses, the pacemaker thus stimulates the heart at the rate set by the atrial escape interval or the sum of the atrial escape interval and the AV delay, respectively, i.e., upon the timing-out of each atrial and/or ventricular escape interval. When the hysteresis mode is enabled, sensed cardiac activity causes the pacemaker escape interval to be extended, or lengthened, thereby providing a longer period of time within which natural cardiac activity may occur before the pacemaker steps in to generate a stimulation pulse. Should the intrinsic rate of the heart fall below the programmed hysteresis rate, i.e., should no intrinsic cardiac activity be sensed during the lengthened escape interval, then a stimulation pulse is generated, and the escape interval reverts back to its initial value, as determined by the programmed minimum rate.

Further intervals set to determine the pacemaker's behavior include refractory periods like a post ventricular refractory period (PVARP), which is started with delivery of a ventricular pacing pulse and during which no atrial activity is sensed thus rendering the pacemaker refractory (insensitive) in the atrium during PVARP. This interval and other intervals will not be discussed further herein since these intervals are understood by one skilled in the art.

A stimulation pulse to the myocardium only causes capture of a respective heart chamber, if the myocardium of that chamber is not in a refractory state and if the stimulation pulse strength is above the capture threshold of said myocardium. A sub-threshold stimulation pulse will not cause capture even if delivered to the myocardium in its non-refractory state. Capture only occurs if a stimulation pulse is strong enough to cause excitation of the myocardium. Pulse strength depends both on duration and amplitude of an electrical stimulation pulse. Usually, stimulation pulse strength is adjusted by adjusting the pulse amplitude while maintaining the pulse duration.

The stimulation pulse strength just enough to cause capture of a heart chamber is called capture threshold. It is desirable to adjust the stimulation pulse strength so that the stimulation pulse strengths for particular heart chambers just above capture threshold in order to spend as little energy as possible for a single stimulation pulse while ensuring reliable effectiveness of a stimulation pulse delivered.

Since capture threshold may vary from heart chamber to heart chamber and from patient to patient and may even very over time, there is a need for automatic capture testing and determination in particular as far as implantable heart stimulators are concerned.

In order to determine whether a stimulation pulse has led to capture or not, the number of approaches are used. One approach is to detect characteristic signal pattern in an electrocardiogram originating from a particular heart chamber wherein the characteristic signal pattern corresponds to an evoked response. An alternative approach is to time the delivery of the stimulation pulse such that the stimulation pulse would precede an intrinsic contraction of the heart chamber by a small amount of time. Such stimulation pulse renders the myocardium of the heart chamber refractory. In its refractory period, the heart chamber is not sensitive to any stimulus or intrinsic excitation. Therefore, a stimulation pulse delivered just before a natural contraction of the heart chamber occurs should suppress the natural contraction of the heart chamber. On the other hand, if the stimulation pulse is ineffective, one could sense a natural contraction of the heart chamber shortly after delivery of said stimulation pulse.

In a rhythm based capture detection as for example described in US Patent application 2005/0222630, for purpose of atrial capture detection the atrium is stimulated with an overdrive pacing rate which is higher than the intrinsic atrial rate for a predetermined number of heart cycles. Capture is detected when the number of sensed intrinsic atrial events is smaller than effort of the predetermined number of heart cycles stimulated with the overdrive pacing rate. Loss of capture is detected when the number of sensed atrial events within a set period of time of stimulating the atrium with the overdrive pacing rate is larger than the number of stimulated atrial heart cycles stimulated with the overdrive pacing rate.

For at least the limitations described above there is a need for an atrial heart stimulator apparatus and method.

BRIEF SUMMARY OF THE INVENTION

One or more embodiments of an atrial heart stimulator apparatus and method will now be briefly described. Embodiments of the invention enable improved atrial capture detection in the atrium. A further object of embodiments of the invention is to improve atrial capture threshold detection in the atrium. These objectives are achieved in embodiments of the invention by a heart stimulator comprising:

an atrial stimulation pulse generator being connected to or capable of being connectable to an atrial pacing electrode, wherein the atrial stimulation pulse generator is adapted to generate atrial stimulation pulses having an adjustable strength, a ventricular stimulation pulse generator connected to or capable of being connectable to a ventricular pacing electrode, an atrial sensing channel comprising an atrial sensing unit adapted to process an electrical signal originating from an atrium of a heart and to detect atrial depolarization/contraction events and to put out an atrial sense signal upon detection of an atrial event, a ventricular sensing channel comprising a ventricular sensing unit adapted to process an electrical signal originating from a ventricle of a heart and to detect ventricular depolarization/contraction events and to put out a ventricular sense signal upon detection of a ventricular event, and a control unit connected to the atrial stimulation pulse generator, the ventricular stimulation pulse generator, the atrial sensing channel and the ventricular sensing channel. According to embodiments of the invention, the control unit is adapted to adjust the atrial stimulation pulse strength and to perform an automatic atrial capture threshold test comprising triggering a sequence of a predetermined number of Y atrial stimulation pulses in a ventricular event based inhibited mode with an overdrive rate (ODR) being higher than an intrinsic heart rate and counting the number X of atrial sense events corresponding to the sequence of Y atrial stimulation pulses.

The ventricular event based inhibited mode is a DDI mode, wherein the basic interval is a V-V interval. The ventricular escape interval is started by any ventricular event, regardless of whether intrinsic or paced, and thus is a V-Vp interval. The atrial escape interval also is started by any ventricular event, regardless whether intrinsic or paced, and thus is a V-Ap interval According to embodiments of the invention, this kind of pacing mode is used during automatic atrial capture threshold test even if the pacemaker otherwise operates in an atrial based DDD mode as outlined above wherein the basic interval is an A-A interval and the ventricular escape interval is an A-Vp interval and the atrial escape interval is a A-Ap interval.

Thus, during automatic atrial capture threshold test each atrial stimulation pulse of the sequence atrial stimulation pulses is triggered by a timeout of a respective atrial escape interval unless the atrial escape interval is reset prior to timeout and triggering of an atrial stimulation pulse is inhibited. Also, during automatic atrial capture threshold test each escape interval (both, atrial and ventricular escape intervals) is started by a ventricular sensed or paced event (ventricle triggered escape interval).

As one mode of operation during automatic atrial capture threshold test is an inhibited mode of operation, the control unit is adapted during automatic atrial capture threshold test to reset any atrial escape interval and inhibit delivery of an atrial stimulation pulse at the end of the ventricle triggered atrial escape interval upon receiving an atrial sense signal from the atrial sense channel prior to timeout of the atrial escape interval.

The overdrive-pacing rate (ODR) is approximately 20% higher than a sensed intrinsic heart rate (RR-rate) in one or more embodiments of the invention. Corresponding to the overdrive pacing (or stimulation) rate is an overdrive interval (ODI) that also corresponds to the ventricular escape interval. The overdrive interval is the reciprocal value of the overdrive rate (ODI=1/ODR) and equals the ventricular escape interval during atrial capture threshold test. One skilled in the art will recognize that this exemplary rate of 20% may be adjusted to be any number higher than the sensed intrinsic heart rate in keeping with the spirit of the invention.

The control unit may be adapted in one or more embodiments to reset an atrial escape interval during automatic atrial capture threshold test also upon receiving a ventricular sense signal from the ventricular sense channel prior to timeout of said atrial escape interval. Thus, the atrial escape interval is reset by either an atrial sense event or the ventricular sense event.

Regarding counting of atrial sense events during automatic atrial capture threshold test it is preferred although not required that the control unit does not to count any atrial sense event (As) in an interval beginning right after a first sensed atrial event (As1) having caused inhibition of an atrial stimulation pulse and ending with a first atrial stimulation pulse (Ap1) following the first atrial sense event (As1).

With respect to counting atrial sense events during automatic atrial capture threshold test it is further preferred but not required that the control unit does not count any atrial sense event (As) in an interval beginning right after a first sensed atrial event (As1) occurring in a post ventricular refractory period (PVARP) and ending with the atrial escape interval and the delivery of the atrial stimulation pulse (Ap).

Thus, if an escape As or escape Vs causes inhibition of the Ap, any following events (before the next Ap) are ignored for classification purpose. An atrial sense in a test cycle is counted toward LOC (Loss Of Capture) only if a pair of test Ap-Vp precedes it. Only one atrial sense is counted per test cycle. This prevents exogenous noise and atrial extra-systole from causing a LOC miss-classification on a particularly noisy single interval.

One or more embodiments of the control unit detects capture for a sequence of atrial stimulation pulses (Ap) having all the same adjusted stimulation pulse strength if the number X of atrial sense events (As) corresponding to the number Y of atrial stimulation pulses in said sequence of atrial stimulation pulses is smaller than Y/3. One skilled in the art will recognize that other fractional values differing from this exemplary value may be utilized in keeping with the spirit of the invention.

Likewise it is preferred but not required that the control unit detects loss of capture for sequence of atrial stimulation pulses (Ap) having all the same adjusted stimulation pulse strength if the number X of atrial sense events (As) corresponding to the number Y of atrial stimulation pulses in said sequence of atrial stimulation pulses is equal or larger than Y/3.

Thus, during automatic atrial capture threshold test for any specific atrial stimulation pulse strength to be tested, the atrium is stimulated for a test window of Y cycles (preferable Y=5) at the calculated overdrive stimulation (pacing) rate ODR. LOC is detected if atrial senses are counted in X (preferable X=2) test cycles of all cycles in the test window. Otherwise, capture (CAP) is detected.

It is further preferred but not required that the control unit also triggers ventricular stimulation pulses during automatic atrial capture threshold test (not only atrial stimulation pulses). Each ventricular stimulation pulse is triggered at timeout of a respective ventricular escape interval (V-Vp) unless a ventricular sense event (Vs) resets the ventricular escape interval (V-Vp) prior to timeout and thus inhibits triggering of a ventricular stimulation pulse (Vp), each ventricular escape interval during automatic atrial capture threshold test is started by a ventricular sense event (Vs) or a ventricular stimulation pulse (Vp).

In one or more embodiments, the control unit schedules the ventricular escape interval (V-Vp) such that it ends at a programmable time between 50 ms and 70 ms after timeout of the atrial escape interval (V-Ap). Because of the short Ap-Vp interval, the right ventricle is also overdriven for Y cycles.

Furthermore, it is preferred that the control unit is adapted to reschedule the next following ventricular escape interval after an atrial sense event during an atrial escape interval so that a scheduled time interval (Ap-Vp) between timeout of the next atrial escape interval and timeout of the next ventricular time interval is maintained and the time interval (As-Ap) between the atrial sense event (As) and the timeout of the next atrial escape interval (V-Ap) equals the cycle length (ODI) of the overdrive rate. Thus, after an escape As, the following Ap-Vp pair is rescheduled so that the As-Ap interval equals to the cycle length of ODR. By this means, the algorithm can regain ODR control of the atrial rhythm and maintain the A-V synchrony in DDI mode.

In order to confirm adequacy of a found capture threshold level the control unit is preferably adapted to perform a credibility test for a found capture threshold level, wherein the control unit triggers a first test sequences of atrial stimulation pulses (Ap+) with an atrial stimulation pulse strength being 0.3V higher than the found capture threshold level and a second test sequence of atrial stimulation pulses (Ap−) with an atrial stimulation pulse strength set to for example 0.3V lower than the found capture threshold level, wherein the control unit accepts the found capture threshold level if the control unit has detected capture for the first test sequence and loss-of-capture for the second sequence.

It is preferred but not required that the heart stimulator performs atrial based (atrium controlled) DDD-mode stimulation of a heart instead of a ventricular based DDD-mode (see above). Use of atrial based DDD-mode for example occurs even if during automatic atrial capture threshold test the timing of the escape intervals is controlled by ventricular events.

The present invention is equally applicable to all other electro stimulation devices such as biventricular three chamber pacemakers or implantable cardioverters and defibrillators.

BRIEF DESCRIPTION OF THE DRAWINGS

The above and other aspects, features and advantages of the invention will be more apparent from the following more particular description thereof, presented in conjunction with the following drawings wherein any element in any of the following drawings as shown and described below may be utilized in combination with any other element in any other drawing.

DETAILED DESCRIPTION

An atrial heart stimulator apparatus and method will now be described. In the following exemplary description numerous specific details are set forth in order to provide a more thorough understanding of embodiments of the invention. It will be apparent, however, to an artisan of ordinary skill that the present invention may be practiced without incorporating all aspects of the specific details described herein. In other instances, specific features, quantities, or measurements well known to those of ordinary skill in the art have not been described in detail so as not to obscure the invention. Readers should note that although examples of the invention are set forth herein, the claims, and the full scope of any equivalents, are what define the metes and bounds of the invention.

Figure 1:
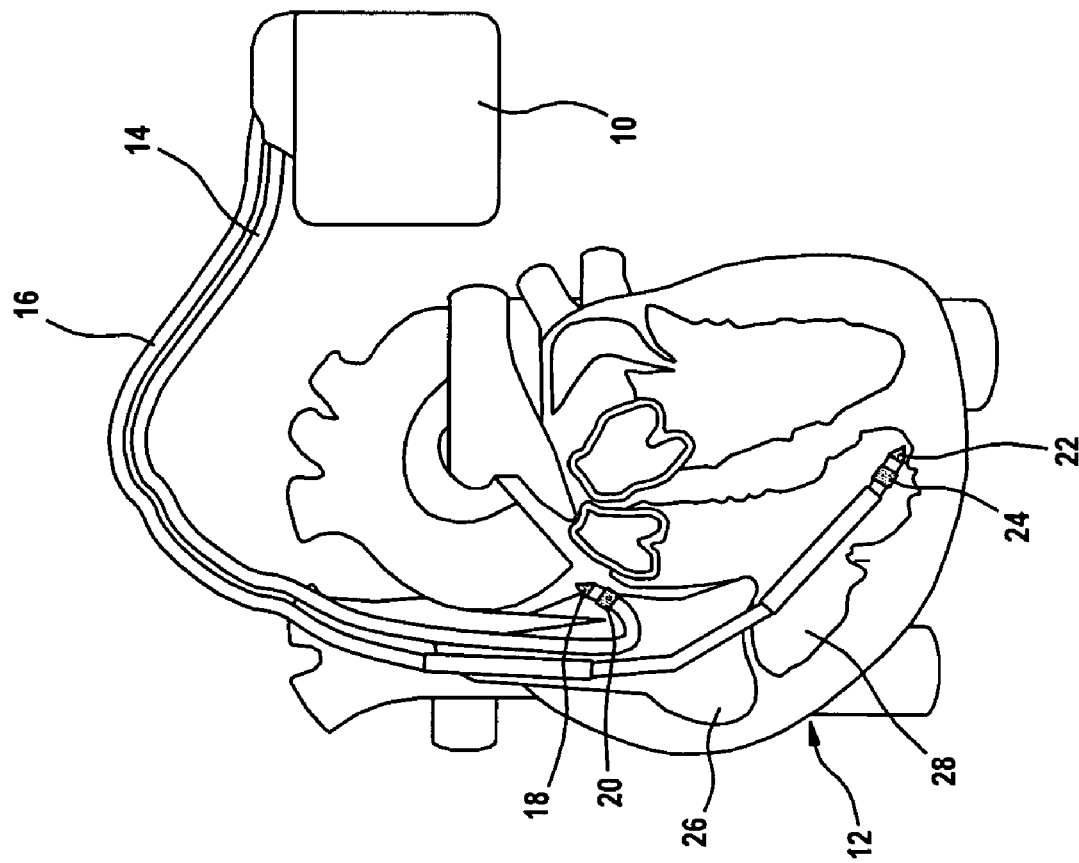
FIG. 1 shows a dual chamber pacemaker connected to pacing/sensing leads placed in a heart.

Referring to FIG. 1, the heart stimulator is a dual chamber pacemaker 10 connected to pacing/sensing leads placed in heart 12 is illustrated. Pacemaker 10 is coupled to heart 12 by way of leads 14 and 16, lead 14 having a pair of right atrial electrodes 18 and 20 that are in contact with right atria 26 of heart 12, and lead 16 having a pair of electrodes 22 and 24 that are in contact with right ventricle 28 of heart 12. Electrodes 18 and 22 are tip-electrodes at the distal end of leads 14 and 16 respectively. Specifically, electrode 18 is a right atrial tip electrode RA-Tip and electrode 22 is a right ventricular tip electrode 22. Electrodes 20 and 24 are designed as ring electrodes in close proximity but electrically isolated from respective tip electrodes 18 and 22. Electrode 20 forms a right atrial tip electrode RA-Ring and electrode 24 forms a right ventricular ring electrode RV-Ring.

Figure 2:
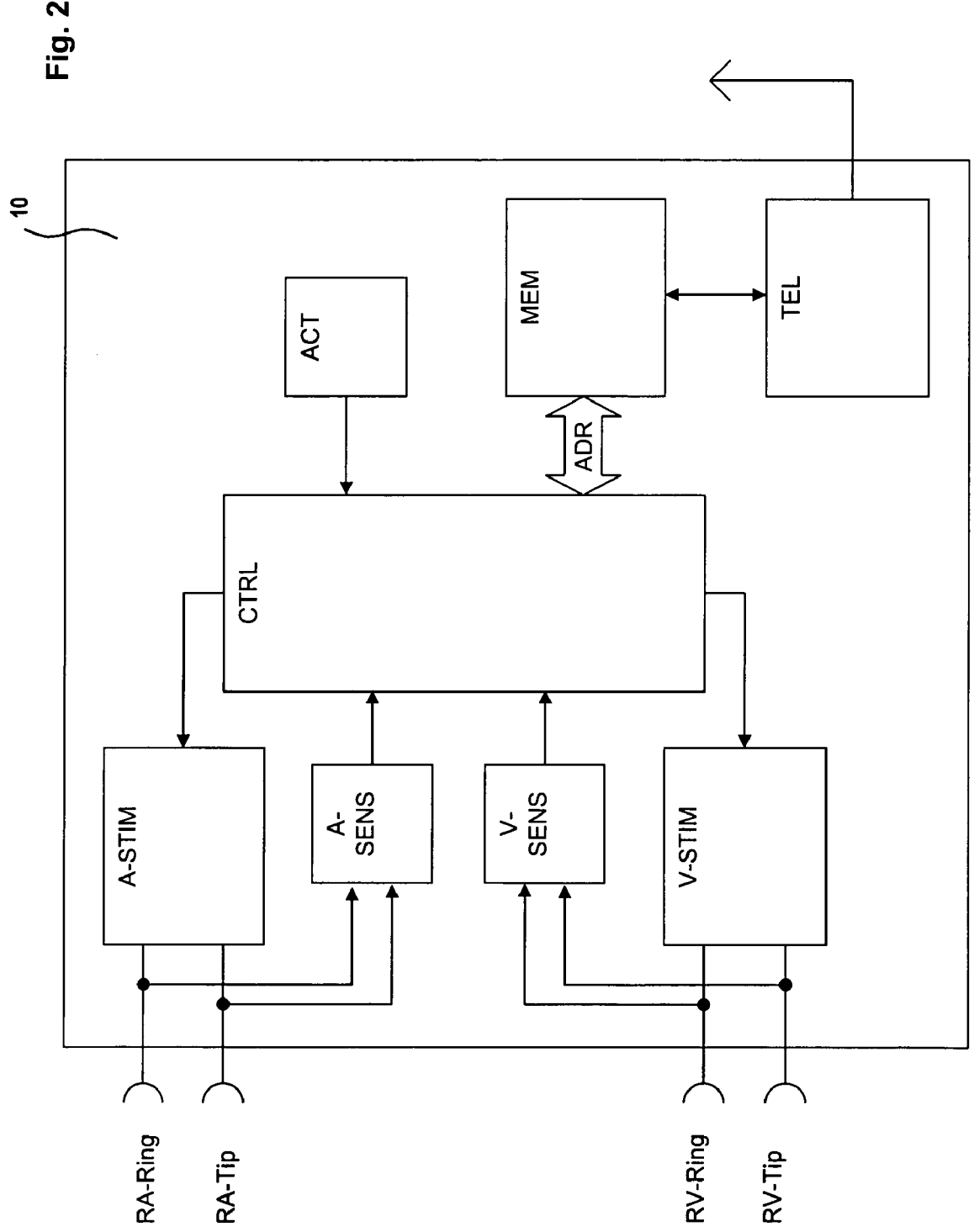
FIG. 2 shows a block diagram of a rate-responsive pacemaker as depicted in FIG. 1.

Referring to FIG. 2 a block diagram of a dual chamber pacemaker 10 is illustrated. During operation, leads 14 and 16 are connected to respective output/input terminals of pacemaker 10 as indicated in FIG. 1 and carry stimulating pulses to tip electrodes 18 and 22 from an atrial stimulation pulse generator A-STIM and a ventricular pulse generator V-STIM respectively. Further, electrical signals from the atria are carried from the electrode pair 18 and 20, through the lead 14, to the input terminal of an atrial channel sense amplifier A-SENSE; and electrical signals from the ventricles are carried from the electrode pair 22 and 24, through the lead 16, to the input terminal of a ventricular sense channel amplifier R-SENSE, also known as V-SENSE.

Controlling the dual chamber pacer 10 is a control unit CTRL, which is connected to the sense amplifiers A-SENSE and V-SENSE and to the stimulation pulse generators A-STIM and V-STIM. Control unit CTRL receives the output signals from the atrial sense amplifier A-SENSE and from the ventricular sense amplifier V-SENSE. The output signals of sense amplifiers A-SENSE and V-SENSE are generated each time that a P-wave or an R-wave, respectively, is sensed within heart 12.

Control unit CTRL also generates trigger signals that are sent to atrial stimulation pulse generator A-STIM and ventricular stimulation pulse generator V-STIM, respectively. These trigger signals are generated each time that a stimulation pulse is to be generated by the respective pulse generator A-STIM or V-STIM. The atrial trigger signal is referred to simply as the "A-pulse", and the ventricular trigger signal is referred to as the "V-pulse". During the time that either an A-pulse or V-pulse is being delivered to the heart, the corresponding sense amplifier, A-SENSE and/or R-SENSE (or V-SENSE), is typically disabled by way of a blanking signal presented to these amplifiers from the control unit CTRL, respectively. This blanking action prevents the sense amplifiers A-SENSE and V-SENSE from becoming saturated from the relatively large stimulation pulses that are present at their input terminals during this time. This blanking action also helps prevent residual electrical signals present in the muscle tissue as a result of the pacer stimulation from being interpreted as P-waves or R-waves.

Still referring to FIG. 2, pacer 10 may also include a memory circuit MEM that is coupled to the control unit CTRL over a suitable data/address bus ADR. This memory circuit MEM allows certain control parameters, used by the control unit CTRL in controlling the operation of pacemaker 10, to be programmably stored and modified, as required, in order to customize the pacemaker's operation to suit the needs of a particular patient. Such data includes the basic timing intervals used during operation of the pacemaker. Further, data sensed during the operation of the pacer may be stored in the memory MEM for later retrieval and analysis.

A telemetry circuit TEL is further included in the pacemaker 10. This telemetry circuit TEL is connected to the control unit CTRL by way of a suitable command/data bus. Telemetry circuit TEL allows for wireless data exchange between pacemaker 10 and any remote programming or analyzing device which can be part of a centralized service center serving multiple pacemakers.

Pacemaker 10 in FIG. 1 is referred to as a dual chamber pacemaker because it interfaces with both the right atrium 26 and the right ventricle 28 of the heart 10. Those portions of the pacemaker 10 that interface with the right atrium, e.g., the lead 14, the P-wave sense amplifier A-SENSE, the atrial stimulation pulse generator A-STIM and corresponding portions of the control unit CTRL, are commonly referred to as the atrial channel. Similarly, those portions of pacemaker 10 that interface with right ventricle 28, e.g., lead 16, R-wave sense amplifier V-SENSE, ventricular stimulation pulse generator V-STIM, and corresponding portions of control unit CTRL, are commonly referred to as the ventricular channel.

In order to allow rate adaptive pacing in a DDDR mode, pacemaker 10 further includes a physiological sensor ACT that is connected to control unit CTRL of pacemaker 10. While this sensor ACT is illustrated in FIG. 2 as being included within pacemaker 10, it is to be understood that the sensor may also be external to pacemaker 10, yet still be implanted within or carried by the patient. A common type of sensor is an activity sensor, such as a piezoelectric crystal, mounted to the case of the pacemaker. Other types of physiologic sensors may be used, such as sensors that sense the oxygen content of blood, respiration rate, pH of blood, body motion, and the like. The type of sensor used is not critical to the present invention. Any sensor capable of sensing some physiological parameter relatable to the rate at which the heart should be beating can be used. Such sensors are commonly used with "rate-responsive" pacemakers in order to adjust the rate of the pacemaker in a manner that tracks the physiological needs of the patient.

Embodiments of the methods of the pacemaker shall now be described. The methods are achieved by adapting control unit CTRL to behave as described hereinafter, for example with CTRL configured with executable program code.

For the purpose of this disclosure, the following abbreviations and definitions are used:

A: Any atrial event whether it is a sensed atrial event corresponding to an intrinsic atrial contraction or whether it is an atrial stimulation pulse, also called atrial pace event.

As: An atrial sense event corresponding to an intrinsic (natural) atrial contraction, that is not stimulated.

Ap: An atrial pace event that is an atrial stimulation pulse delivered to the atrium regardless whether the atrial pace event causes capture or not.

V: Any ventricular event including ventricular pace events and ventricular sense events.

Vs: A ventricular sense event (intrinsic ventricular contraction).

Vp: A ventricular pace event that is a stimulus delivered to the ventricle of super threshold or sub threshold strengths.

ODR: Overdrive rate, a (ventricular) stimulation rate being higher than an intrinsic heart rate.

ODI: Overdrive interval, that is the interval corresponding to the overdrive rate (ODI=1/ODR); the overdrive interval corresponds to the ventricular escape interval during automatic atrial capture threshold test.

VAI: The atrial escape interval during automatic atrial capture threshold test since the atrial escape interval is a VA interval.

PVARP: Post Ventricular Atrial Refractory Period, that is a period of time beginning with a ventricular pace event during which no atrial sense events are recorded for further evaluation.

CAP: Capture signal indicating that the control unit has detected capture as result of an automatic atrial capture threshold test.

LOC: A loss-of-capture signal generated by the control unit at the end of an automatic atrial capture threshold test if the control unit has detected loss of capture.

Figure 3:
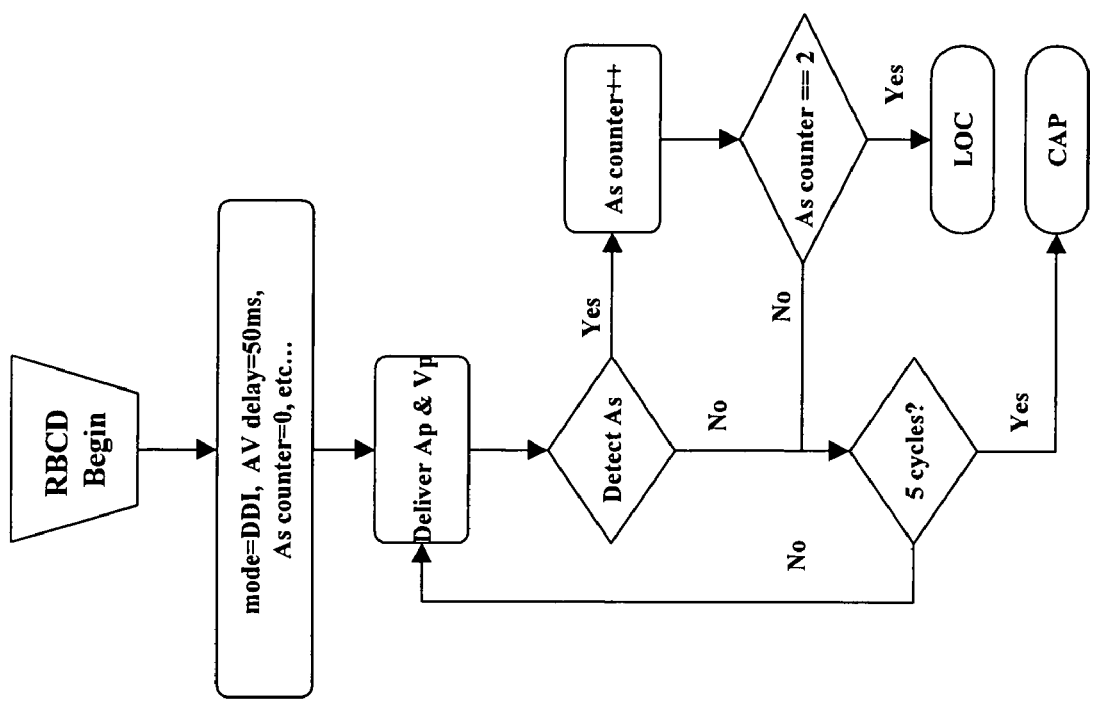
FIG. 3 is a flow chart illustrating an embodiment of a method utilized by the control unit and thus the pacemaker during automatic atrial capture threshold test.

As shown in FIG. 3, during automatic atrial capture threshold test, control unit CTRL triggers a sequence of five ventricle started atrial escape intervals (VAI) and ventricular escape intervals with an overdrive pacing rate ODR being about 20 percent higher than an intrinsic heart rate. One skilled in the art will recognize that any rate higher than intrinsic heart rate may be utilized in keeping with the spirit of the invention and the 20 percent figure is exemplary only. Thus, the ventricular escape interval corresponds to the overdrive interval ODI being determined by the overdrive rate by ODI=1/ODR). The mode of operation during automatic atrial capture threshold test is a ventricular based DDI mode in one or more embodiments of the method. A fixed AV delay (time difference between the timeout of an atrial escape interval and timeout of the concurring ventricular escape interval) of 50 ms is maintained during automatic atrial capture threshold test for example.

During automatic atrial capture threshold test, control unit CTRL triggers an atrial stimulation pulse Ap (corresponding to an atrial pace event) and a ventricular stimulation pulse Vp, respectively, at the end of the atrial escape interval and the ventricular escape interval unless triggering of the stimulation pulse is inhibited by a sense event prior to timeout of the atrial or the ventricular escape interval, respectively. Any sense event (that is, both, atrial and ventricular sense events) resets the atrial escape interval and thus inhibits triggering of an atrial stimulation pulse. On the other hand, the ventricular escape interval only is reset by a ventricular sense event Vs during a ventricular escape interval. An atrial sense event As during post ventricular refractory period PVARP is not recorded and thus cannot reset the atrial escape interval. However, such atrial sense event AsPmt during PVARP can be counted for capture detection purpose.

For the purpose of capture detection atrial sense events As during automatic atrial capture threshold tests are counted. Should an atrial sense event As during atrial escape interval VAI or a ventricular sense event Vs during VAI cause inhibition of an atrial stimulation pulse Ap, any following event until the next atrial stimulation pulse Ap is ignored and not counted for capture detection purpose. An atrial sense event As during automatic atrial capture threshold test is only counted if a pair of an atrial stimulation pulse Ap and a subsequent ventricular stimulation pulse Vp without any intermediate event precedes the atrial sense event As to be counted. A norm atrial sense event As is counted test cycle (during one overdrive interval). Thus, exogenous noise and atrial extrasystoles are excluded from being counted and leading to misdetection of loss of capture. Control unit CTRL generates a loss of capture signal (LOC) at the end of an automatic atrial capture threshold test if the number of counted atrial sense events As is equal or is larger than a predetermined number X. For a total number of 5 test cycles during automatic atrial capture threshold test, a preferred number for X is 2. Thus, if control unit CTRL counts two or more atrial sense events As within five cycles of the ventricular based DDI pacing with an overdrive rate ODR, loss of capture is detected and a LOC signal is generated. Otherwise, if control unit CTRL only detects one atrial sense event or no atrial sense event or no atrial sense event within said five cycles, capture is detected and control unit CTRL generates a CAP signal. Other numbers of pulses and sense events may be used in keeping with the spirit of the invention and the use of 5 and 2 respectively is exemplary only.

Figure 4:
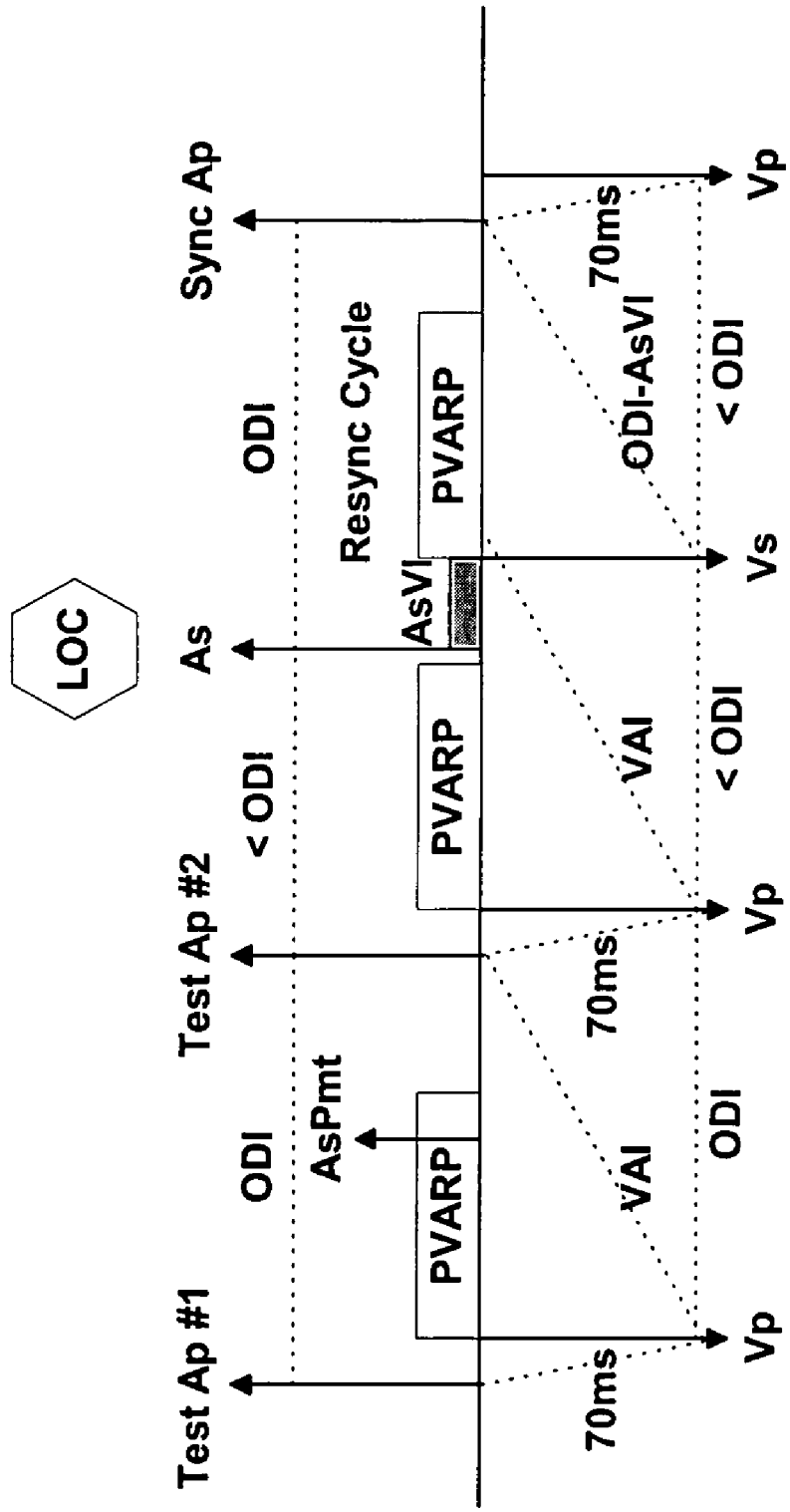
FIG. 4 shows a timing diagram of atrial and ventricular events during automatic atrial capture threshold test in case of loss of capture.
Figure 5:
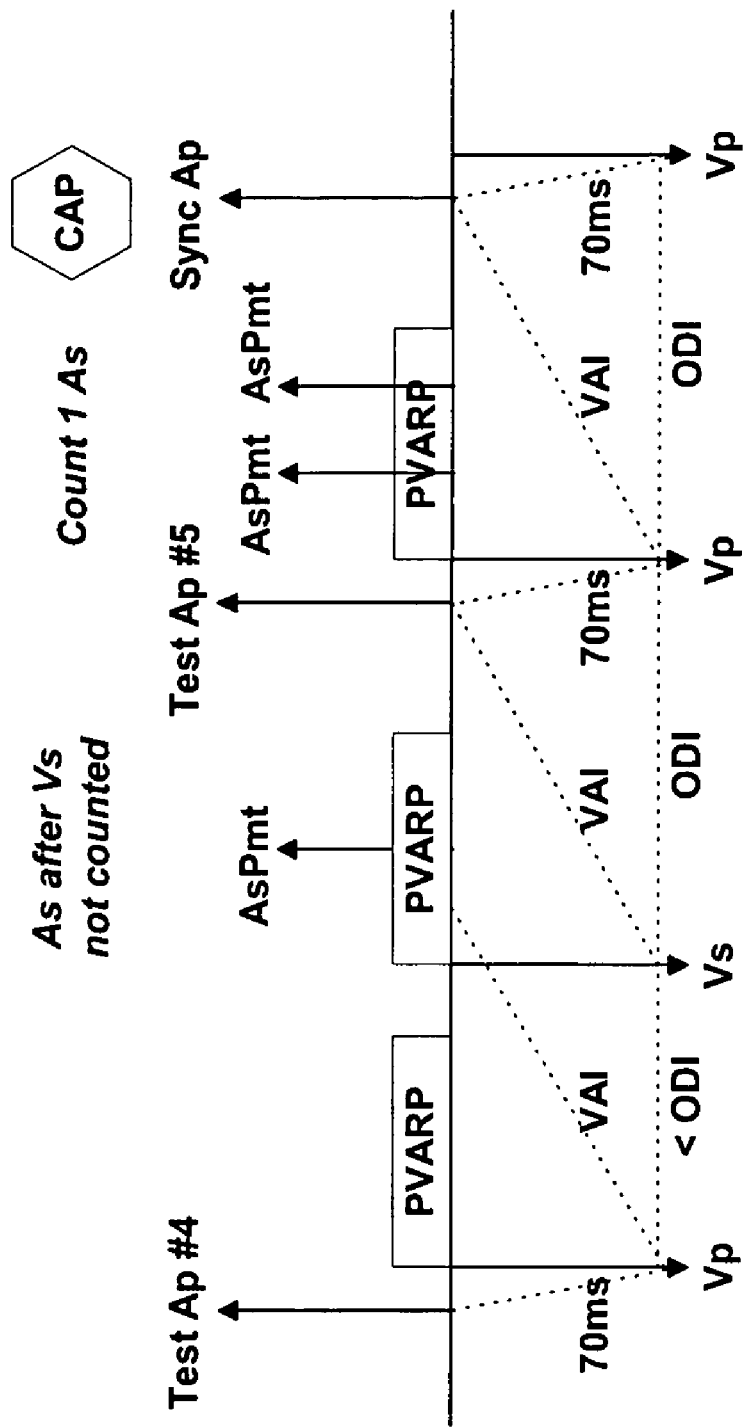
FIG. 5 shows a timing diagram of atrial and ventricular events during automatic atrial capture threshold test in case of capture.

An example for a typical sequence of atrial and ventricular events during automatic atrial capture threshold test in case of loss of capture is depicted in FIG. 4. FIG. 5, conversely shows sequence of atrial and ventricular events which lead to detection of capture.

The principal behind this kind of rate based capture detection is, as pointed out earlier, that a supra threshold atrial stimulation pulse Ap delivered outside the atrial refractory period causes the atrium to capture and thus will render the atrium refractory for a predetermined period of time. In the refractory state, the atrium is not susceptible to any atrial excitation whether intrinsic or stimulated. Thus, an intrinsic atrial contraction can be suppressed by a preceding supra threshold atrial stimulation pulse. On the other hand, a sub threshold atrial stimulation pulse having too little a pulse strength to cause capture does not render the atrium refractory and thus is not capable to suppress the next intrinsic atrial contraction. Thus, in case of a sub threshold atrial stimulation pulse an atrial sense event may be detected after delivery of said sub threshold atrial stimulation pulse. In order to make sure that an atrial stimulation pulse Ap of a pulse strength to be tested is delivered prior to an intrinsic atrial contraction, both, ventricle and atrium of the heart, are stimulated with the overdrive-pacing rate being higher than the natural, intrinsic heart rate. Furthermore, the time interval between timing out of the atrial escape interval and the ventricular escape interval set to a short, fixed value of preferably 50 ms to maximize the possibility of exposing atrial sense events As after delivery of a sub threshold atrial stimulation pulse Ap. Other embodiments may use any other time interval such as 70 ms for example. Furthermore, a short Ap-Vp interval prevents a retrograde activation of the atrium by a ventricular stimulation pulse Vp, if the atrial stimulation pulse Ap to be tested is of (supra threshold) pulse strength causing the atrium to capture. FIG. 4 shows that AsPmt is ignored during PVARP and an As occurring out of PVARP is counted and causes a Resync cycle to occur. FIG. 5 shows that an AsPmt is not counted after a Vs without a corresponding As as per the middle cycle and that only 1 AsPmt is counted during a PVARP as per the final cycle.

Figure 6:
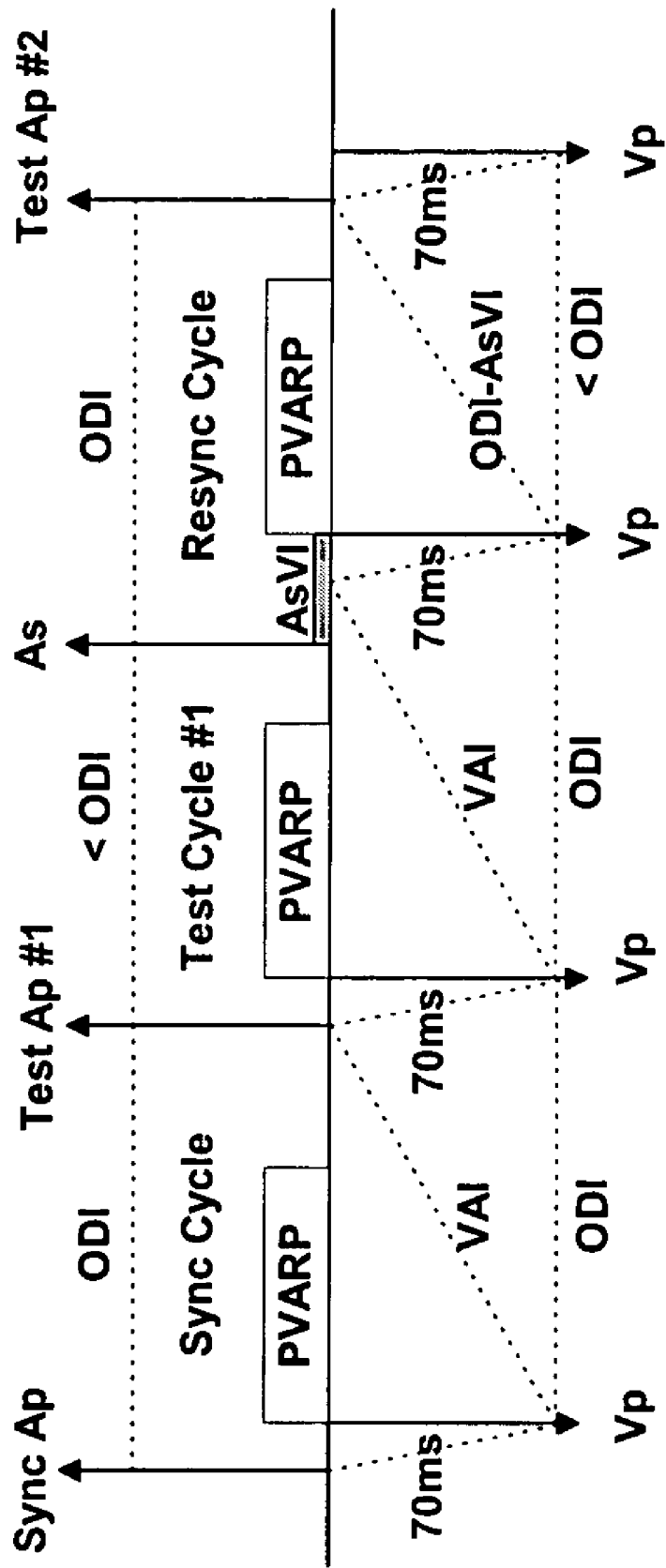
FIG. 6 shows a timing diagram of atrial and ventricular events when the ventricular based timing is rescheduled due to an atrial sense event during automatic capture threshold test.

In order to maintain an acceptable atrial ventricular synchrony in DDI mode during overdrive-rate pacing, control unit CTRL reschedules a ventricular escape interval in response to an atrial sense event As during atrial escape interval. The ventricular escape interval in this case is rescheduled so that the interval from the sensed atrial event As to timeout of the next atrial escape interval equals to the overdrive-interval ODI while maintaining the interval between timeout of the atrial escape interval and the simultaneous ventricular escape interval of 50 ms. This kind of rescheduling of the ventricular escape interval in case of an atrial sense event is depicted in FIG. 6.

Although an exemplary embodiment of the present invention has been shown and described, it should be apparent to those of ordinary skill in the art that a number of changes and modifications of the invention may be made without departing from the spirit and the scope of the invention. In which particular, rhythm based atrial capture detection as disclosed herein is also applicable by ventricular pacemakers which are capable to stimulate left ventricle in addition to the right ventricle. Furthermore, the invention is applicable to implantable cardioverter defibrillators. This invention can readily be adapted to such device by following the present teachings. All such changes, modifications and alterations should therefore be recognized as falling within the scope of the present invention that only is limited by the wording of the claims. While the invention herein disclosed has been described by means of specific embodiments and applications thereof, numerous modifications and variations could be made thereto by those skilled in the art without departing from the scope of the invention set forth in the claims.

What is claimed is:

1. A heart stimulator comprising:
    an atrial pacing electrode;
    an atrial stimulation pulse generator coupled with the atrial pacing electrode, said atrial stimulation pulse generator configured to generate atrial stimulation pulses having an adjustable strength;
    a ventricular pacing electrode;
    a ventricular stimulation pulse generator coupled with the ventricular pacing electrode;
    an atrial sensing channel comprising an atrial sensing unit configured to process an electrical signal originating from an atrium of a heart and to detect atrial depolarization/contraction events and to output an atrial sense signal upon detection of an atrial event selected from said atrial depolarization/contraction events;
    a ventricular sensing channel comprising a ventricular sensing unit configured to process an electrical signal originating from a ventricle of said heart and to detect ventricular depolarization/contraction events and to output a ventricular sense signal upon detection of a ventricular event selected from said ventricular depolarization/contraction events; and,
    a control unit being coupled with said atrial stimulation pulse generator, said ventricular stimulation pulse generator, said atrial sensing channel and said ventricular sensing channel wherein said control unit is configured to adjust atrial stimulation pulse strength and to perform an automatic atrial capture threshold test wherein said atrial capture threshold test is configured to trigger a sequence of a predetermined number of Y atrial stimulation pulses in a ventricular event based inhibited mode with an overdrive rate set higher than an intrinsic heart rate of said heart and wherein said atrial capture threshold test is further configured to count a number X of atrial sense events corresponding to said sequence of said predetermined number of Y atrial stimulation pulses, wherein Y is greater than one and wherein X is equal to or greater than zero and is less than or equal to Y and wherein X is compared to a predetermined threshold to determine either capture or loss of capture.

2. The heart stimulator of claim 1 wherein said control unit is configured to perform said automatic atrial capture threshold test wherein each atrial stimulation pulse of said sequence of said predetermined number of Y atrial stimulation pulses is triggered by a timeout of a respective atrial escape interval unless said atrial escape interval is reset prior to timeout and thus a trigger of an atrial stimulation pulse is inhibited.

3. The heart stimulator of claim 2 wherein said control unit is configured to reset an atrial escape interval during said automatic atrial capture threshold test upon receiving said atrial sense signal from said atrial sense channel prior to timeout of said atrial escape interval.

4. The heart stimulator of claim 1 wherein said control unit is configured to perform said automatic atrial capture threshold test wherein each escape interval is started by a ventricular sensed or paced event.

5. The heart stimulator of claim 1 wherein said control unit is configured to reset an atrial escape interval during said automatic atrial capture threshold test upon receiving said ventricular sense signal from said ventricular sense channel prior to timeout of said atrial escape interval.

6. The heart stimulator of claim 1 wherein said control unit is configured to not count any atrial sense event As in an interval beginning directly after a first sensed atrial event As1 having caused inhibition of an atrial stimulation pulse and ending with a first atrial stimulation pulse Ap1 following said first atrial sense event As1.

7. The heart stimulator of claim 1 wherein said control unit is configured to not count any atrial sense event As in an interval beginning directly after a first sensed atrial event As1 occurring in a post ventricular refractory period PVARP and ending with an atrial escape interval and a delivery of a atrial stimulation pulse Ap.

8. The heart stimulator of claim 1 wherein said control unit is configured to detect capture for said sequence of said predetermined number of Y atrial stimulation pulses Ap having a same adjusted stimulation pulse strength if said number X of atrial sense events As corresponding to said sequence of said predetermined number of Y of atrial stimulation pulses is smaller than Y/3.

9. The heart stimulator of claim 1 wherein said control unit is configured to detect loss of capture for said sequence of said predetermined number of Y atrial stimulation pulses Ap having a same adjusted stimulation pulse strength if said number X of atrial sense events As corresponding to said sequence of said predetermined number of Y atrial stimulation pulses is greater than or equal to Y/3.

10. The heart stimulator of claim 1 wherein said control unit is configured to trigger ventricular stimulation pulses during said automatic atrial capture threshold test wherein each ventricular stimulation pulse is triggered at timeout of a respective ventricular escape interval V-Vp unless a ventricular sense event Vs resets a ventricular escape interval V-Vp prior to said timeout and thus inhibits triggering of a ventricular stimulation pulse Vp wherein each ventricular escape interval during said automatic atrial capture threshold test is started by said ventricular sense event Vs or said ventricular stimulation pulse Vp.

11. The heart stimulator of claim 10 wherein said control unit is configured to schedule said ventricular escape interval V-Vp such that said ventricular escape interval V-Vp ends at a programmable time between 50 ms and 70 ms after timeout of an atrial escape interval V-Ap.

12. The heart stimulator of claim 1 wherein said control unit is configured to reschedule a next ventricular escape interval after an atrial sense event during an atrial escape interval so that a scheduled time interval Ap-Vp between timeout of said next atrial escape interval and timeout of said next ventricular time interval is maintained and a time interval As-Ap between said atrial sense event As and said timeout of said next atrial escape interval V-Ap equals a cycle length ODI of said overdrive rate.

13. The heart stimulator of claim 1 wherein said control unit is configured to set said overdrive rate ODR to be 20% higher than said intrinsic heart rate Vs-Vs of said heart.

14. The heart stimulator of claim 1 wherein said control unit is configured to perform a credibility test for a found capture threshold level, wherein said control unit triggers a first test sequence of atrial stimulation pulses Ap+ with an atrial stimulation pulse strength being 0.3V higher than a found capture threshold level and a second test sequence of atrial stimulation pulses Ap– with an atrial stimulation pulse strength being 0.3V lower than said found capture threshold level, wherein said control unit accepts said found capture threshold level if said control unit has detected capture for said first test sequence and loss-of-capture for said second sequence.

15. The heart stimulator of claim 1 wherein said control unit is configured to perform atrial based DDD-mode stimulation of said heart outside said automatic atrial capture threshold test, wherein in said atrial based DDD-mode both atrial escape intervals and ventricular escape intervals, are started synchronously by an atrial sense event or an atrial stimulation pulse.

* * * * *